United States Patent
Camerlengo

(10) Patent No.: US 7,018,389 B2
(45) Date of Patent: Mar. 28, 2006

(54) EMULSIFICATED TIP FOR OCULISTIC SURGERY, PARTICULARLY FOR PHACOEMULSIFICATION OF CATARACT

(75) Inventor: Flavio Camerlengo, Rome (IT)

(73) Assignee: Optikon 2000 S.p.A., (IT)

( * ) Notice: Subject to any disclaimer, the term of this patent is extended or adjusted under 35 U.S.C. 154(b) by 356 days.

(21) Appl. No.: 10/021,685

(22) Filed: Dec. 11, 2001

(65) Prior Publication Data

US 2002/0072754 A1    Jun. 13, 2002

(30) Foreign Application Priority Data

Dec. 11, 2000    (IT)    ................. RM20000229 U

(51) Int. Cl.
*A61B 17/32*    (2006.01)

(52) U.S. Cl. ...................... 606/166; 606/167

(58) Field of Classification Search ........ 606/166–170, 606/4–6, 107, 181; 604/22, 200, 244, 272
See application file for complete search history.

(56) References Cited

U.S. PATENT DOCUMENTS

| | | | |
|---|---|---|---|
| 3,906,954 A | | 9/1975 | Baehr et al. |
| 4,008,976 A | * | 2/1977 | Holzl ..................... 408/144 |
| 4,014,333 A | * | 3/1977 | McIntyre ................. 604/43 |
| 4,525,417 A | | 6/1985 | Dimigen et al. |
| 4,531,934 A | | 7/1985 | Kossovsky et al. |
| 4,556,607 A | * | 12/1985 | Sastri ..................... 428/627 |
| 4,981,756 A | | 1/1991 | Rhandhawa |
| 5,788,679 A | * | 8/1998 | Gravlee, Jr. ............. 604/272 |
| 5,993,408 A | | 11/1999 | Zaleski |
| 6,028,387 A | | 2/2000 | Boukhny |
| 6,056,764 A | * | 5/2000 | Smith ..................... 606/167 |
| 6,217,584 B1 | * | 4/2001 | Nun ....................... 606/107 |

FOREIGN PATENT DOCUMENTS

| | | |
|---|---|---|
| CH | 621476 | 2/1981 |
| FR | 2592063 | 6/1987 |

OTHER PUBLICATIONS

Esteve et al., "Mechanical and Tribological Properties of Tungsten Carbide Sputtered Coatings", Superfaces Y Vacio, vol. 9, 1999, pp. 276-279. XP002265428.

Hoffman A et al., "Compaction, Distribution, and Chemical Bonding of Tungsten-Implanted Glassy Carbon", Journal of Applied Physics, American Institute of Physics. New York, US, vol. 72, No. 12, Dec. 15, 1992, pp. 5687-5694. XP001172409. ISSN: 0021-8979.

Harry et al., "Adhesion and Failure Mechanisms of Tungsten-Carbon Containing Multilayered and Graded Coatings Subjected To Scratch Tests", Thin Solid Films, Elsevier-Sequoia S.A. Lausanne, CH, vol. 342, No. 1-2, Mar. 26, 1999, pp. 207-213, XP004168096. ISSN: 0040-6090.

* cited by examiner

*Primary Examiner*—(Jackie) Tan-Uyen T. Ho
(74) *Attorney, Agent, or Firm*—Gauthier & Connors LLP

(57) ABSTRACT

The invention concerns an improved tip (1) for oculistic surgery, particularly for the removal of cataract, having a proximal joint end (2) and a distal end (4), contacting the crystalline during the surgical intervention, wherein the distal end (4) contacting a corneal or sclera tissue is coated with an anti-friction treatment, based on carbon and tungsten carbide.

5 Claims, 1 Drawing Sheet

EMULSIFICATED TIP FOR OCULISTIC SURGERY, PARTICULARLY FOR PHACOEMULSIFICATION OF CATARACT

BACKGROUND OF THE INVENTION

1. Field of the Invention

The invention relates to an improved tip for oculistic surgery, particularly for the removal of cataract by the cataract "phacoemulsification" technique.

2. Description of the Prior Art

More particularly, the invention concerns a tip of the above kind to be used in the ultrasound phacoemulsification technique with a 1 mm incision.

As it is well known, the "phacoemulsifier" substantially is an instrument comprised of a control unit and a "handle", by which the surgeon makes the intervention.

At the end of the handle, a "needle" or "tip" is coupled, oscillated at a ultrasonic frequency by a "piezoelectric" or "magneto-restrictive" system, housed within the same "handle".

"Handle" is further provided with an infusion and suction system, the first one of which generally acts by gravity, while the second latter is assisted by a vacuum pump.

Suction system is realised in such a way to act coaxially through the needle and is useful to suck the crystalline (cataract), crushed by the vibratory motion of the same needle.

Instead, the infusion system acts concentrically and outside the needle, irrigating within the eye a physiological solution to restore the liquid sucked along with the crystalline.

Particularly, the irrigation passes through the annular space created by a small "sleeve", generally comprised of silicone, coaxially placed outside the needle.

In the "traditional" technique, the needle—sleeve assembly is introduced within the "front chamber" of the eye, by a corneal incision having dimensions proportional to the diameter of the needle (2.5–3 mm).

Present trend in cataract "phacoemulsification" is that of reducing at most the extension of the corneal incision, in order to minimise the surgical trauma (post surgical astigmatism, etc.).

This was possible thanks to the evolution of foldable lenses replacing the crystalline, requiring corneal incisions always smaller to be implanted.

One of the most recent surgical techniques following this tendency is that providing the irrigation separated from the needle and carried out by a suitable cannula introduced within the eye through a second corneal incision.

This technique allows employing very small phacoemulsification tips, without irrigation sleeve, requiring very much reduced corneal incisions (1 mm).

It is well evident that two opposed incisions of 1 mm, are less traumatic for the corneal tissue than one incision of 3 mm; furthermore, said "bimanual" technique give to the surgeon a best action capability.

One of the complications that could occur employing said surgical technique is the more or less marked burning of the cornea in correspondence of the two incision flaps though which the needle passes, due to the heat generated by friction caused by the friction of the needle against the cornea.

To aggravate the problem contributes the movements of the needle, made by the surgeon transversely with respect to the corneal incision.

Up today, very few are the solutions trying to solve said complication acting on the needle dynamic friction coefficient, said needle being comprised of 5 grade titanium alloy, due to mechanical needing.

In this situation, it is well evident how it could be advantageous a valid solution that would give remarkable advantages in case of "via pars-plana" phacoemulsification, a kind of intervention by which the crystalline is reached from the rear part of the ocular bulb through the sclera, since for said intervention longer and thinner needles are employed, without irrigation sleeve.

A first solution, already suggested, is that of carrying out a better surface finishing (polishing) of the part of the needle that could contact the corneal incision.

Limits of said solution are due to the fact that, even obtaining a certain reduction of the friction coefficient, it is bound to the kind of material (5 grade titanium alloy) used to manufacture the needle.

A subsequent solution already suggested in the art, and subject of the Italian Patent Application No. RM97U000159, filed on Jul. 30, 1997 in the name of Optikon 2000 S.p.A., provides a partial coating of the needle by PTFE.

The last solution, even if remarkably reduces the dynamic friction coefficient between needle and cornea, has remarkable drawbacks.

PTFE deposition method, particularly in the titanium alloy by which the needle is realised, does not guarantee a good adhesion; thus, the coating easily separates, particularly close to the transition zone between coating and anti-reflex treatment.

Always due to the PTFE deposition method, thickness of the coating is not uniform and in any case is often rather high with respect to the needle dimensions, thus causing an increase of the outer diameter of the same of about 400 μm, that is disadvantageous for its use.

Finally, PTFE coating, which is particularly soft, is not so much resistant to mechanical stresses (abrasion, scratch, etc.) to which it can be subjected during its use.

SUMMARY OF THE INVENTION

All the above makes the PTFE coated needles delicate and little lasting, even if they are at the beginning efficient to reduce the corneal burnings.

In view of the above, the Applicant has realised a solution able to solve all the problems of the known solutions.

Main object of the present invention is that of realising a particular needle set to be used on the crushing and suction ultrasonic devices for different kind of materials (organic and non-organic), for all cases where the needle is in contact with structure to be maintained.

It is therefore specific object of the present invention an improved tip for oculistic surgery, particularly for the removal of cataract, having a proximal joint end and a distal end, contacting the crystalline during the surgical intervention, wherein the distal end contacting a corneal or sclera tissue is coated with an anti-friction treatment, based on carbon and tungsten carbide.

Preferably, according to the invention, said treatment is carried out by a PVD (Physical Vapour Deposition) technique.

Furthermore, according to the invention, a thin layer of chromium ($Cr_1$) is applied during said treatment, to improve the adhesion of the subsequent depositions.

Still according to the invention, said proximal joint end is subjected to polishing.

Always according to the invention, said end is shaped with different angles and geometry.

BRIEF DESCRIPTION OF THE DRAWINGS

The present invention will be now described, for illustrative but not limitative purposes, according to its preferred embodiments, with particular reference to the figures of the enclosed drawings, wherein.

DETAILED DESCRIPTION OF THE INVENTION

As it can be noted from the enclosed figures, a tip 1, or needle, according to the invention, can be ideally divided into three zones, respectively from the right to left end in the figures, a first zone 2, provided with threads for the coupling with the handle, a second zone 3, having a bigger thickness, and partially conically shaped, and a third zone 4, or terminal end of the tip 1, having a lower diameter and conically shaped.

Figure 1:
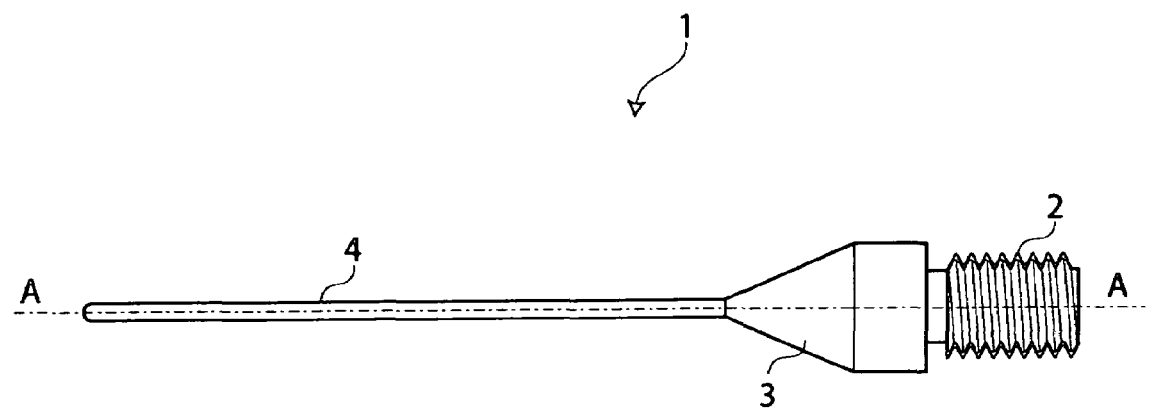
FIG. 1 is a lateral view of a tip according to the invention.
Figure 2:
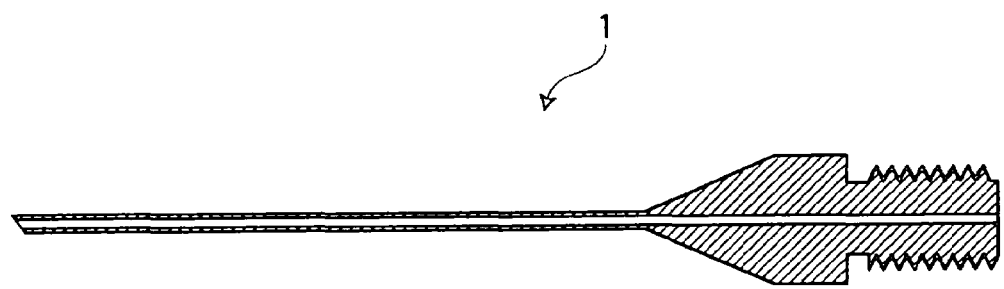
FIG. 2 is section view of the tip of FIG. 1.

By the solution suggested according to the present invention, it is proposed the realisation of a particular set of tips or needles 1 to be employed on crushing and suction ultrasonic oscillatory devices, for different materials (organic and non organic), for all those cases where the needle 1 is in direct contact (zone 4, FIG. 1) with structures to be maintained.

The solution according to the invention particularly provides needles 1 preferably comprised of 5 grade titanium alloy (Ti6A14V), that up today cannot be coated by an anti-friction coating having said features, wherein the zone 4 contacting organic structures (cornea, sclera, etc.) to be maintained is coated by a particular treatment LFC (WC/C) with low friction coefficient.

Particularly, it is a multilayer amorphous coating, comprised of tungsten carbide and carbon, applied under vacuum employing a modified PVD technique, in function of the particular application.

Due to the particular geometry of the needles 1 according to the invention, i.e. a very little and long hole, a specific preparation method has been studied (pickling, cleaning and drying) guaranteeing a perfect cleaning before the deposition method.

The deposition method of the tungsten carbide has been modified for the particular application, depositing a thin chromium (Cr1) substrate (by PVD evaporation), in order to improve the adhesion of the following WC and WC/C depositions.

By this kind of technology, a biocompatible coating is obtained, having optimum adhesion features (90+/−5 N Scratch Test), high hardness (1200 HV), a low friction coefficient (0,08+/−0,01 Ra), with a total thickness of about 2 micrometers.

The above mentioned coating must preferably involve zone 4 of the needle, since, even if no contra-indications exists to extend the coating on the zone 3, it is not advisable to extend the same to avoid to jeopardise couplings with handle and unscrewing wrench.

Consequently, the mechanical finishing (polishing) of zone 3 is more convenient, in order to reduce cavitation turbulences. Said zone never contacts cornea or sclera.

Therefore, by the solution suggested according to the present invention, a needle is obtained for the removal of crystalline by phacoemulsification, with a bimanual technique (separated irrigation), providing an outer surface having the features shown in the figure, with a polished joint portion 3 and an end part 4 coated with a particular anti-friction LFC treatment.

The present invention has been described for illustrative but not limitative purposes, according to its preferred embodiments, but it is to be understood that modifications and/or changes can be introduced by those skilled in the art without departing from the relevant scope as defined in the enclosed claims.

What is claimed is:

1. A tip for oculistic surgery, particularly for the removal of a cataract, said tip having a proximal joint end and a distal end, which contacts crystalline during a surgical intervention, wherein the distal end which contacts a corneal or sclera tissue is coated with an anti-friction treatment, based on carbon and tungsten carbide.

2. The tip according to claim 1, wherein said treatment is carried out by a PVD (Physical Vapour Deposition) technique.

3. The tip according to claim 1, wherein a thin layer of chromium ($Cr_1$) is applied during the treatment, to improve adhesion of the subsequent depositions.

4. The tip according to claim 1, wherein said proximal joint end is subjected to polishing.

5. The tip according to claim 1, wherein said end is shaped with different angles and geometry.

* * * * *